United States Patent [19]
Little et al.

[11] 3,965,187
[45] June 22, 1976

[54] HYDROGENATION OF PHENOL
[75] Inventors: Edwin D. Little, Convent Station; Zafarullah K. Cheema, Morris Township, N.J.
[73] Assignee: Allied Chemical Corporation, New York, N.Y.
[22] Filed: July 2, 1970
[21] Appl. No.: 52,129

[52] U.S. Cl. .................. 260/586 R; 260/621 A; 260/621 C; 260/624 A
[51] Int. Cl.² ........................................ C07C 45/00
[58] Field of Search ........ 260/586 R, 621 C, 624 A, 260/621 A

[56] References Cited
UNITED STATES PATENTS

| 2,737,480 | 3/1956 | Adams et al. | 260/621 |
| 2,886,601 | 5/1959 | Clough | 260/624 |
| 3,029,294 | 4/1962 | Keeble | 260/621 |
| 3,076,810 | 2/1963 | Duggan et al. | 260/586 |
| 3,187,050 | 6/1965 | Duggan et al. | 260/621 A |

OTHER PUBLICATIONS

Higgins Plant, Hercules Powder Company (1955) 211d pg. of "The Inside Story".

"Chemical Reviews" vol. 63 (1963) Layer pp. 490–493.

Primary Examiner—James O. Thomas, Jr.
Assistant Examiner—A. Siegel
Attorney, Agent, or Firm—Roger H. Criss; Michael S. Jarosz

[57] ABSTRACT

The catalytic hydrogenation of phenol obtained by the cumene hydroperoxide process is improved by hydrogenating high purity phenol containing not more than 75 ppm of acetol, an impurity found in phenol prepared from cumene. Acetol-free phenol is obtained by treating phenol for 1–5 minutes with a polyamine such as hexamethylene diamine, hexamethylene triamine and the like or an aqueous solution thereof, and then distilling the mixture to separate the components. Alternatively, the hydrogenability of phenol can be improved by injecting the polyamine into the reaction mixture during hydrogenation.

5 Claims, No Drawings

HYDROGENATION OF PHENOL

This invention relates to the catalytic hydrogenation of phenol.

The process whereby phenol is hydrogenated to cyclohexanol or directly and selectively to cyclohexanone is well known. It is also well-known that certain impurities present in commercial phenol affect the hydrogenation process. For example, the presence of iron, sulfur, and halogen has been known to reduce catalyst efficiency and adversely affect selectivity.

In an effort to overcome these problems, the prior art has suggested the use of special catalysts and has further suggested certain pretreatment purification techniques prior to hydrogenation. None of these have met with too great a success, even though phenol having a purity of 99.9% is obtainable. One reason for this lack of success is that the exact role played by the impurities present in phenol is not clear. In this respect it should be noted that impurities present in phenol when used in one commercial application such as the preparation of phenolic resins are not particularly significant in hydrogenation procedures. Accordingly, certain of the impurities which affect color stability of phenol do not affect the hydrogenability of phenol, and vice versa. Another reason for this lack of success is that commercial phenol is derived from a variety of sources and the impurities contained therein are of process environmental origin. Thus phenol obtained from the distillation of coal tar, or from the hydrolysis of chlorobenzene or from the dehydrogenation of cyclohexanol or cyclohexanone will contain impurities which are different from those contained in phenol prepared by the cumene hydroperoxide process. In addition, not only will the nature and quantity of contaminants vary with the source, but they will also vary from batch to batch when prepared by the same process. This is particularly true with phenol obtained by the decomposition of cumene hydroperoxide.

The present invention obviates these problems by providing an improved method for hydrogenating phenol wherein the effectiveness of the catalyst is greatly prolonged and hydrogenation rate increased.

SUMMARY OF THE INVENTION

An object of the present invention is provision of an improved process for hydrogenating phenol obtained by the decomposition of cumene hydroperoxide using standard hydrogenation catalysts and conditions, the improvement residing in effecting the hydrogenation in the substantial absence of acetol (an impurity which is also formed with phenol when the latter is prepared by the cumene hydroperoxide process, and which has been found to be a catalyst poison). Another object of the present invention is to provide a process for improving the hydrogenability of phenol obtained by the decomposition of cumene hydroperoxide which comprises removing acetol by first treating the phenol having a purity of at least 99.8% with a polyamine.

DESCRIPTION OF THE INVENTION

We have found that the single most detrimental impurity contributing to the poisoning of catalyst systems when phenol is hydrogenated, is a specific carbonyl compound formed along with phenol by decomposition of cumene hydroperoxide. This specific carbonyl compound is known as 1-hydroxy-2-propanone, hydroxyacetone or acetol. More specifically, we have found that when phenol is hydrogenated in the presence of acetol, the effectiveness of a hydrogenation catalyst is greatly reduced. This reduction of effectiveness is noted in two ways, firstly, in that the hydrogenation rate is decreased, and secondly, in that the catalyst life is greatly diminished. Accordingly, the present invention relates to an improved method for hydrogenating phenol, which is obtained by the decomposition of cumene hydroperoxide, using hydrogen and standard hydrogenation conditions and catalysts, to form cyclohexanone and cyclohexanol, the improvement residing in effecting the hydrogenation while employing phenol having a purity of at least 99.8% and an acetol content not greater than 75, and preferably 0–30 ppm. According to another embodiment of the present invention there is provided a method for improving hydrogenability of phenol obtained by the decomposition of cumene hydroperoxide which comprises removing acetol by first treating phenol having a purity of at least 99.8% with a polyamine and then distilling the mixture to separate the amine and the acetol impurity from the phenol.

As has been previously indicated, when cumene hydroperoxide is decomposed with an acid catalyst, the mixture thus obtained contains among the identifiable products phenol, acetone, toluene, mesityl oxide, acetol, alpha-methylstyrene, and methyl benzofuran. Analysis of separate production runs of crude phenol obtained by the decomposition of cumene hydroperoxide show that these impurities occur in amounts which vary from one production lot to the next.

Upon further investigation into the effects that these impurities may have upon the hydrogenation of phenol, acetol was found to be the single most detrimental impurity of the known impurities to hydrogenation of phenol. Other impurities which affect color stability of phenol, such as methyl benzofuran, and mesityl oxide, have little effect on hydrogenation even when the former is present in amounts of about 1400 ppm. The linear relationship between acetol content and hydrogenation time is shown in Table I wherein a high purity phenol was hydrogenated before and after the addition of acetol.

TABLE I

| Impurities | Fractionally Distilled Phenol | Acetol Additions No. 1 | Acetol Additions No. 2 |
|---|---|---|---|
| Acetone | 760 ppm | 717 ppm | 19 ppm |
| Toluene | 13 " | 13 " | 0 " |
| Mesityl Oxide | 0 " | 0 " | 26 " |
| Acetol | 33 " | 331 " | 465 " |
| Alpha-Methylstyrene | 30 " | 32 " | 34 " |
| Methyl-Benzofuran | 61 " | 61 " | 108 " |
| Total | 897 ppm | 1154 ppm | 652 ppm |
| Hydrogenation Time | 1 hr. 30 min. | 3 hr. 00 min. | 3 hr. 40 min. |

The hydrogenability of phenol can be improved in many ways. For example, the acetol content of a particular phenol may be reduced by subjecting the phenol to fractional distillation through a spinning band column. In this process phenol is purified by fractionation through an angular "Teflon" spinning band distillation column under atmospheric pressure and at a 4:1 reflux ratio. Alternatively, acetol content may be diminished by recrystallization, that is, a procedure which involves melting phenol in a heated vessel with stirring and then allowing partial crystallization to occur while maintaining the temperature at 40.5°–41°C. for about 3 hours. The crystalline slurry is then filtered under vacuum at 42°C. and the filtrate again subjected to slow crystallization process for at least 5 times. In another procedure acetol may be diminished by treating with inorganic acid (i.e. sulfuric or phosphoric acid) and then a base (i.e. sodium hydroxide or sodium carbonate) according to the method described in U.S. Pat. No. 3,140,318. Another method for reducing the acetol content of phenol is described in U.S. Pat. No. 2,922,169.

Although the aforementioned procedures will improve the hydrogenability of production grade phenol considerably, acetol may best be removed by treating the phenol with a polyamine followed by distillation to separate the acetol and amine, from the phenol. Alternatively, the polyamine may be injected into the hydrogenator along with the phenol, thereby by eliminating the distillation step. By this particular method it is possible to remove from 88–100% of the acetol present in the phenol.

A wide variety of polyamine compounds can be employed to enhance the hydrogenability of phenol and any polyamine can be used in which the amino groups are primary or secondary and in which no substituents are present which interfere with the reaction. Suitable polyamines include compounds of the formula $$R_1-\overset{H}{\underset{}{N}}-(R-\overset{R_3}{\underset{}{N}})_n-R-\overset{H}{\underset{}{N}}-R_2$$

wherein $n$ is an integer from 0 to 4, preferably 0 to 1, and most preferably 0, $R_1$, $R_2$ and $R_3$ are independently selected from the group consisting of hydrogen; alkyl, preferably 1-10 carbon atoms; aryl, preferably of 6-10 carbon atoms; cycloalkyl, preferably of 4-10 carbon atoms; aralkyl, preferably of 7-20 carbon atoms and alkaryl preferably of 7-20 carbon atoms, and R, which may be the same or different in different

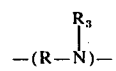

groups, is a member selected from the group consisting of alkylene, preferably of 1–40 carbon atoms; arylene, preferably of 6–10 carbon atoms; alkylenearylene, preferably of 7–20 carbon atoms; dialkylenearylene, preferably of 7–20 carbon atoms; cycloalkylene, preferably of 4–10 carbon atoms; dialkylene cycloalkylene, preferably of 6–20 carbon atoms; nitrogen containing heterocyclic groups of 5–6 carbon atoms and the lower alkyl substituted, hydroxy substituted and carboxyl substituted derivatives of the above listed radicals. $R_1$, $R_2$ and $R_3$ are preferably all hydrogen, and R is preferably alkylene or arylene, including lower alkyl, hydroxy or carboxyl substituted derivatives thereof. The alkyl and alkylene groups in these polyamine compounds may be straight-chain, branched-chain or cyclic. These polyamines may be used in the form of a single compound, as a mixture of isomers, or as a mixture of polyamines containing from 2 to 6 amino nitrogen atoms in the molecule. Additionally the amines may be used in aqueous media containing up to 75% water. Illustrative of suitable polyamines are: ortho, meta and para-xylylenediamine; ortho, meta and para-toluylenediamine; hexamethylene diamine; ortho, meta and para-phenylenediamine; 4,5-diaminoxylene; 3,5-diaminobenzoic acid; 3,4-diaminobenzoic acid; 2,6-diaminopyridine; 1,5-diaminonaphthaline; 1,2-diaminonaphthline; 1,5-diaminopentane; 1,4-cyclohexanebis(methylamine); N-(3-aminopropyl)cyclohexylamine; N-phenylethylenediamine; 1,3-diamino-2-hydroxypropane; diethylene triamine; di-n-propylene triamine; di-i-butylene triamine; di-n-hexylene triamine; triethylene tetramine; tri-i-propylene tetramine; tri-n-hexylene tetramine; 4-(2-aminoethyl)-diethylene triamine; tetraethylene pentamine; tetra-n-propylene pentamine; tetra-n-butylene pentamine; pentaethylene hexamine; and amines of the formula

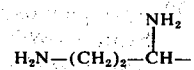

$$H_2N-(CH_2)_2-\overset{NH_2}{\underset{}{C}H}-(CH_2)_{16}-CH_3,\ H_2N-(CH_2)_2-\overset{NH_2}{\underset{}{C}H}-(CH_2)_{18}-CH_3\ \text{and}\ H_2N-R^1-NH_2$$

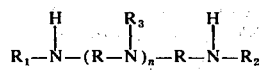

where R is an aliphatic hydrocarbon chain of 36 carbon atoms.

The polyamine interacts with or binds the acetol present in such a manner that phenol free of the acetol impurity can be recovered by distillation. The amount of polyamine compound required is, to some extent, dependent upon the concentration of acetol present in the phenol. In general, the amount of polyamine used is about 0.01–2.0%; preferably about 0.03–1.0% based on the weight of the phenol.

The exact temperature at which the phenol is treated with the polyamine compound is not critical. Generally, the treatment is carried out at a temperature of 40°–220°C. and preferably 60°–200°C. The time of the treatment should be long enough to permit the desired reaction to take place. In general, substantial reaction can be obtained in one minute with a minimum time of about 5 minutes being preferred.

The distillation whereby the phenol is freed from the ketonic impurities can be carried out at atmospheric pressure, reduced pressure or super-atmospheric pressure. Preferably, distillation is carried out at atmospheric pressure or reduced pressure at a temperature of 80°–182°C. depending upon the pressure in the system.

In hydrogenating phenol according to the present invention, the particular process steps or conditions are not critical. As has been previously stated, the prior art adequately teaches many methods for hydrogenating phenol under varying reaction conditions and employing numerous catalysts systems and all of these are employable in the present invention. For example, the prior art indicates that phenol can be catalytically hydrogenated in the liquid or vapor phase at temperatures ranging from 24°–400°C. and at pressures ranging from 0 to 5000 p.s.i. Similarly, a variety of catalysts and catalyst supporting systems have been satisfactorily employed and any of the conventional hydrogenation catalysts are employable in the present invention. Exemplary of but few of these catalysts are nickel, platinum, cobalt, chromium oxide, palladium, and catalysts comprising mixtures of nickel, chromium, copper and molybdenum.

The aforementioned catalysts have been employed in amounts ranging from 0.5 to 10 percents, suspended in a liquid or supported on external surfaces (pellet or powder) of aluminum oxide, silica acid, diatomaceous earth, charcoal, or Filter Cell, and are present in only minor or catalytic amounts when considering the total catalyst charge in relationship to the total reaction mixture.

Although as previously stated, the particular catalyst and reaction conditions are not critical in the invention, it must be appreciated that certain catalysts are less expensive and more active and selective for hydrogenating phenol directly to cyclohexanone, rather than to cyclohexanol, and it is expected that the choice of a particular catalyst will be governed accordingly. For our purposes, we prefer to use palladium, preferably palladium on carbon, with palladium in amounts ranging from 1–5%. Likewise we prefer to effect the hydrogenation of phenol under conditions the temperature is maintained at about 44°–220°C. and at a pressure of 10 and 300 p.s.i.g., and more preferably at about 150°–200°C. and 100–250 p.s.i. Another especially useful hydrogenation process is set forth in U.S. Pat. No. 2,829,166.

The following examples further illustrate the invention. Example I shows that the acetol content of phenol can be greatly diminished by treatment with meta-xylylenediamine. Examples 2 and 3 illustrate that acetol content can be rapidly reduced or completely eliminated from phenol using meta-xylylene diamine or hexamethylene diamine. Example 4 indicates that hydrogenation time may be decreased without affecting selectively, by hydrogenating phenol in the absence of acetol.

EXAMPLE I

The phenol starting material contained a total of 868 ppm of impurities of which 683 ppm were ketonic (mainly mesityl oxide, acetol and acetophenone). 240 Grams of the phenol and 0.24 grams of m-xylylenediamine (MXDA) were heated for about 15 minutes at 55°–60°C. and distilled at atmospheric pressure. The untreated phenol and the phenol treated with MXDA only, were analyzed. The results are as follows:

|  | Untreated Phenol | MXDA treated |
|---|---|---|
| Impurities (ppm) | 868 | 321 |
| Ketonic impurities (ppm) (mainly acetol) | 683 | 46 |

EXAMPLE 2

Phenol at 165°C. was treated with 0.1%, based on the phenol weight, of meta-xylylenediamine (MXDA) with stirring. Aliquots were removed at various time intervals and chilled to stop any further reactions. The samples were analyzed by gas chromatographic analysis and the results are shown below:

| | Reaction Time, (Mins.) at 165°C. | | | | |
|---|---|---|---|---|---|
| | 0 | 1 | 30 | 120 | 480 |
| Mesityl Oxide | 91 | 82 | 81 | 58 | 37 |
| Acetol | 718 | 43 | 0 | 0 | 0 |
| Acetophenone | 148 | N.C. | 123 | 85 | 88 |
| Total Impurities* | 1133 | 448 | 356 | 288 | 233 |

*Several other impurities are present in low ppm.

EXAMPLE 3

Production phenol (4119 gm) was charged to 5000 ml distillation flask along with 3.2 g. of hexamethylene diamine (4.0g of a 79.8% HMDA in water) and heated to 55°–60°C. One minute after the amine addition a sample was analyzed for impurity content. The results are as follows:

| Sample Impurity | Before HMDA Addition ppm | After HMDA Addition ppm |
|---|---|---|
| Acetone | 7 | 35 |
| Toluene | 4 | 5 |
| Cumene | 0 | 0 |
| Mesityl Oxide | 126 | 78 |
| Acetol | 1459 | 71 |
| α-methylstyrene | 188 | 47 |
| Benzofuran | 55 | 28 |
| Methylbenzofuran | 87 | 74 |
| Acetophenone | 309 | 233 |
| Total | 2235 | 571 |

EXAMPLE 4

A 1 liter autoclave reactor was charged with 900 parts of molten phenol (pretreated according to Example 1) and 2 parts by weight of a finely divided catalyst composed of 5% palladium on charcoal support. The autoclave was maintained at 70 p.s.i. and at a temperature of 150°–190°C. while hydrogen was fed into the reaction mixture at a rate of 0.3 cu. ft. per minute for a period of about 100 minutes. At the end of this time the reactor was discharged, the product filtered to remove catalyst, and analyzed. It was found to be composed on a weight basis of about 0.9% phenol
2.5% cyclohexanol
96.1% cyclohexanone
0.5% high boilers.

When the procedure was repeated using untreated phenol, the hydrogenation time was increased to 170 minutes and the product analyzed as follows:

1.0 phenol
2.7 cyclohexanol
95.9 cyclohexanone
1.1 high boilers.

We claim:

1. In the process for hydrogenating phenol in the presence of hydrogenation catalyst in liquid or vapor phase at temperature of 24° to 400°C., using as starting material phenol having a purity of at least 99.8 percent obtained from fractional distillation of the cumene hydroperoxide decomposition product containing acetol as an impurity, the improvement which comprises: treating said phenol by contact with a polyamine of the formula:

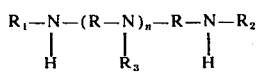

wherein $n$ is an integer from 0 to 4; $R_1$, $R_2$ and $R_3$ are independently selected from the group consisting of hydrogen, alkyl, aryl, cycloalkyl, aralkyl and alkaryl and R independently at each occurrence is selected from the group of radicals consisting of alkylene, arylene, alkylenearylene, dialkylene, cycloaklyene, dialkylene cycloalkylene, nitrogen containing heterocyclic groups of 5 to 6 carbon atoms, and the lower alkyl substituted, hydroxy substituted and carboxyl substituted derivatives of said radicals to reduce its acetol content to a level of less than 75 ppm prior to hydrogenation.

2. The improvement of claim 1 wherein the phenol is treated with 0.01 to 2 percent by weight of said polyamine compound and is distilled to separate the polyamine and acetol.

3. The improvement of claim 2 wherein the phenol is treated with said polyamine compound at a temperature of 40° to 220°C.

4. The method of claim 1 wherein the polyamine compound is hexamethylene diamine.

5. The method of claim 1 wherein the polyamine compound is hexamethylene triamine.

* * * * *

UNITED STATES PATENT AND TRADEMARK OFFICE
CERTIFICATE OF CORRECTION

PATENT NO. : 3,965,187
DATED : June 22, 1976
INVENTOR(S) : Edwin D. Little and Zafarullah K. Cheema It is certified that error appears in the above-identified patent and that said Letters Patent are hereby corrected as shown below:

Col. 5, line 27 add "wherein" after --conditions--

Col. 5, line 41 change "selectively" to --selectivity--

Col. 7, line 10 change "dialkylene" to --dialkylene-arylene--

Signed and Sealed this

Nineteenth Day of April 1977

[SEAL]

Attest:

RUTH C. MASON
*Attesting Officer*

C. MARSHALL DANN
*Commissioner of Patents and Trademarks*